United States Patent [19]

Clark et al.

[11] Patent Number: 5,130,379
[45] Date of Patent: Jul. 14, 1992

[54] HYPOGLYCEMIC THIAZOLIDINEDIONE DERIVATIVES

[75] Inventors: David A. Clark; Steven W. Goldstein; Bernard Hulin, all of Groton, Conn.

[73] Assignee: Pfizer Inc., New York, N.Y.

[21] Appl. No.: 674,833

[22] Filed: Mar. 26, 1991

Related U.S. Application Data

[60] Division of Ser. No. 477,261, Feb. 8, 1990, Pat. No. 5,036,079, which is a continuation-in-part of Ser. No. 428,490, filed as PCT/US88/00733, Mar. 8, 1988, abandoned.

[51] Int. Cl.$^5$ ............... C07D 277/24; C07D 401/14; C07D 403/14; A61K 31/44
[52] U.S. Cl. .................... 514/333; 514/342; 514/369; 546/256; 546/280; 548/183
[58] Field of Search ............ 546/256, 280; 548/110, 548/183; 514/332, 333, 342, 369

[56] References Cited

U.S. PATENT DOCUMENTS

| | | | |
|---|---|---|---|
| 4,287,200 | 9/1981 | Kawamatsu et al. | 514/369 |
| 4,340,605 | 7/1982 | Kawamatsu et al. | 514/342 |
| 4,342,771 | 8/1982 | Schnur | 514/340 |
| 4,367,234 | 1/1983 | Schnur | 514/389 |
| 4,617,312 | 10/1986 | Schnur | 514/369 |
| 4,703,052 | 10/1987 | Eggler et al. | 514/337 |
| 4,725,610 | 2/1988 | Meguro et al. | 514/369 |
| 4,775,687 | 11/1988 | Meguro et al. | 514/369 |

FOREIGN PATENT DOCUMENTS 177353 9/1986 European Pat. Off. ............ 514/369

OTHER PUBLICATIONS

Sohda et al., Chem. Pharm. Bull. Japan, vol. 30, pp. 3580-3600 (1982).

Burger, Alfred, *Medicinal Chemistry*, vol. 3, 3rd Ed., pp. 64-80, Wiley-Interscience (1970).

Primary Examiner—Alan L. Rotman
Attorney, Agent, or Firm—Peter C. Richardson; J. Trevor Lumb; Mervin E. Brokke

[57] ABSTRACT

Hypoglycemic thiazolidine-2,4-dione derivatives wherein
the dotted line represents a bond or no bond;
V is $-CH=CH-$, $-N=CH-$, $-CH=N-$ or S;
W is $CH_2$, CHOH, CO, C=NOR or $-CH=CH-$;
X is S, O, $NR^1$, $-CH=N-$ or $-N=CH-$;
Y is CH or N;
Z is hydrogen, $(C_1-C_7)$alkyl, $(C_3-C_7)$ cycloalkyl, phenyl, naphthyl, pyridyl, furyl, thienyl or phenyl mono- or disubstituted with the same or different groups which are $(C_1-C_3)$alkyl, trifluoromethyl, $(C_1-C_3)$alkoxy, fluoro, chloro or bromo;
$Z^1$ is hydrogen or $(C_1-C_3)$alkyl;
R is hydrogen or methyl; and
n is 1, 2 or 3;

a pharmaceutically acceptble cationic salt thereof; or a pharmaceutically acceptable acid addition salt thereof when the compound contains a basic nitrogen.

37 Claims, No Drawings

HYPOGLYCEMIC THIAZOLIDINEDIONE DERIVATIVES

CROSS REFERENCE TO RELATED APPLICATIONS

This is a division of application Ser. No. 07/477,261, filed on Feb. 8, 1990, U.S. Pat. No. 5,0.6,079 which is a continuation-in-part of application Ser. No. 07,438,490, filed Dec. 7, 1989, abandoned, as a request for U.S. national examination of International application No. PCT/US88/00733, filed Mar. 8, 1988.

BACKGROUND OF THE INVENTION

The present invention relates to certain compounds of the formula (I), depicted below, having utility as hypoglycemic and hypocholesterolemic agents, methods for their use and pharmaceutical compositions containing them.

In spite of the early discovery of insulin and its subsequent wide-spread use in the treatment of diabetes, and the later discovery and use of sulfonylureas (e.g. chlorpropamide, tolbutamide, acetohexamide, tolazamide) and biguanides (e.g. phenformin) as oral hypoglycemic agents, the treatment of diabetes remains less than satisfactory. The use of insulin, necessary in about 10% of diabetic patients in which synthetic hypoglycemic agents are not effective (Type I diabetes, insulin dependent diabetes mellitus), requires multiple daily doses, usually by self injection. Determination of the proper dosage of insulin requires frequent estimations of the sugar in the urine or in the blood. The administration of an excess dose of insulin causes hypoglycemia, with effects ranging from mild abnormalities in blood glucose or coma, or even death. Treatment of non-insulin dependent diabetes mellitus (Type II diabetes) usually consists of a combination of diet, exercise, oral agents, e.g., sulfonylureas, and in more severe cases, insuin. However, the clinically available hypoglycemics are unfortunately fraught with other toxic manifestations which limit their use. In any event, where one of these agents may fail in an individual case, another may succeed. A continuing need for hypoglycemic agents, which may be less toxic or succeed where others fail, is clearly evident.

Furthermore, atherosclerosis, a disease of the arteries, is recognized to be the leading cause of death in the United States and Western Europe. The pathological sequence leading to atherosclerosis and occlusive heart disease has been described in detail by Ross and Glomset in New England Journal of Medicine 295, 369–377 (1976). The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Cholesterol and cholesteryl ester account for most of this lipid. Further, it is postulated that most of the cholesterol found within the fatty streaks results from uptake from the plasma. These fatty streaks, in turn, give rise to development of the "fibrous plaque", which consists of accumulated intimal smooth muscle cells laden with lipid and surrounded by extra cellular lipid, collagen, elastin and proteoglycans. The cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion" which accounts for the the arterial occlusion and tendency toward mural thrombosis and arterial muscular spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at high risk for development or progression of CVD because of this factor. Individuals who possess independent risk factors in addition to hyperlipidemia are at particularly high risk. Such independent risk factors include glucose intolerance, left ventricular hypertrophy hypertension, and being of the male sex. Cardiovascular disease is especially prevalent among diabetic subjects, at least in part because of the existence of multiple independent risk factors. Successful treatment of hyperlipidemia in the general population, and in diabetic subjects in particular, is therefore of exceptional medical importance.

The first step in recommended therapeutic regimens for hyperlipidemia is dietary intervention. While diet alone produces adequate response in some individuals, many others remain at high risk and must be treated further by pharmacological means. New drugs for the treatment of hyperlipidemia are, therefore, of great potential benefit for large numbers of individuals at high risk of developing CVD. Further, successful treatment of both the hyperlipidemia and hyperglycemia associated with the diabetic state with a single therapeutic agent is particularly desirable.

In addition to the hypoglycemic agents cited above, a variety of other compounds have been reported to possess this type of activity, as reviewed by Blank [Burger's Medicinal Chemistry, Fourth Edition, Part II, John Wiley and Sons, N.Y. (1979), pp. 1057-1080].

Schnur, U.S. Pat. No. 4,367,234 discloses hypoglycemic oxazolidinediones of the formula

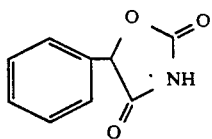

in which the phenyl ring is generally mono- or multi-substituted in the ortho/meta positions. Notably, with the exception of the 4-fluorophenyl analog, the para-substituted derivatives are either inactive or possess a low level of hypoglycemic activity.

Schnur, U.S. Pat. No. 4,342,771 discloses oxazolidinedione hypoglycemic agents of the formula

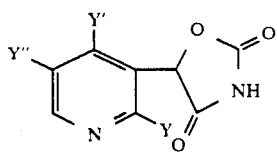

in which Y is hydrogen or alkoxy, Y' is hydrogen or alkyl and Y" is hydrogen or halo.

Schnur, U.S. Pat. No. 4,617,312 discloses hypoglycemic thiazolidinediones of the formula

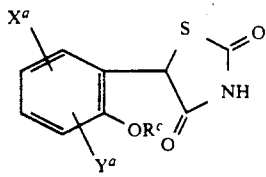

where $R^c$ is lower alkyl, $X^a$ is F, Cl or Br, and $Y^a$ is hydrogen, chloro, lower alkyl or lower alkoxy. Notably, the compounds require ortho-substitution with an alkoxy group, and para-substitution is limited to hydrogen or halogen.

Kawamatsu et al., U.S. Pat. No. 4,340,605, disclose hypoglycemic compounds of the formula

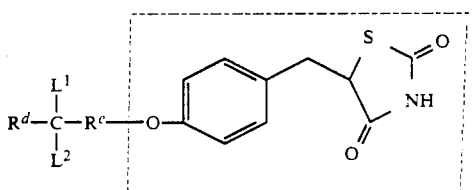

wherein $R^e$ is a bond or lower alkylene and when $R^d$ is an optionally substituted five- or six-membered heterocyclic group including one or two hetero-atoms selected from N, O and S, $L^1$ and $L^2$ may each be defined as hydrogen. Based on on a lack of hypoglycemic and plasma triglyceride lowering activity of certain non-ether analogs, it has been suggested that the boxed portion of the structural formula, including the ether oxygen, represents an essential feature for useful activity in this series of compounds; Sohda et al., Chem., Pharm. Bull. Japan, Vol. 30, pp. 3580-3600 (1982).

Eggler et al., U.S. Pat. No. 4,703,052, disclose hypoglycemic thiazolidinediones of the formula

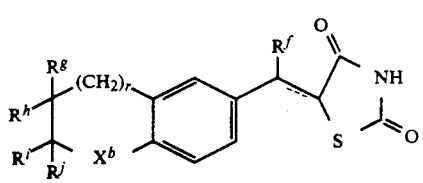

where the dotted line represents an optional bond, $R^f$ is H, methyl or ethyl, $X^b$ is O, S, SO, $SO_2$, $CH_2$, CO, CHOH or $NR^k$, $R^k$ is H or an acyl group and the numerous definitions of $R^g$, $R^h$, $R^i$ and $R^j$ include $R^g$, $R^h$ and $R^i$ as hydrogen or methyl and $R^j$ as optionally substituted phenyl, benzyl, phenethyl or styryl.

SUMMARY OF THE INVENTION

The present invention is directed to compounds having the formula

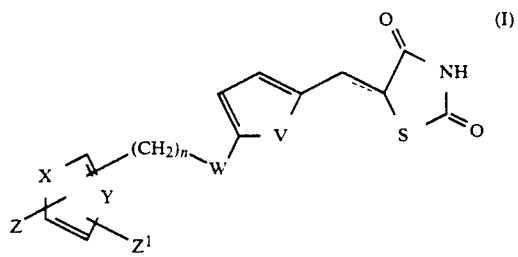

wherein
the dotted line represents a bond or no bond;
V is —CH=CH—, —N=CH—, —CH=N— or S;
W is $CH_2$, CHOH, CO, C=NOR or CH=CH;
X is S, O, $NR^1$, —CH=N— or —N=CH—;
Y is CH or N;
Z is hydrogen, $(C_1-C_7)$alkyl, $(C_3-C_7)$cycloalkyl, phenyl, naphthyl, pyridyl, furyl, thienyl or phenyl mono- or disubstituted with the same or different groups which are $(C_1-C_3)$alkyl, trifluoromethyl, $(C_1-C_3)$alkoxy, fluoro, chloro or bromo;
$Z^1$ is hydrogen or $(C_1-C_3)$alkyl;
R and $R^1$ are each independently hydrogen or methyl; and
n is 1, 2 or 3;
the pharmaceutically acceptable cationic salts thereof; and the pharmaceutically acceptable acid addition salts thereof when the compound contains a basic nitrogen.

Preferred are compounds wherein the dotted line represents no bond, particularly wherein W is CO or CHOH. More preferred are compounds wherein V is —CH=CH—, —CH=N— or S and n is 2, particularly those compounds wherein X is O and Y is N, X is S and Y is N, X is S and Y is CH or X is —CH=N— and Y is CH. In the most preferred compounds X is O or S and Y is N forming an oxazol-4-yl, oxazol-5-yl, thiazol-4-yl or thiazol-5-yl group; most particularly a 2-[(2-thienyl), (2-furyl), phenyl or substituted phenyl]-5-methyl-4-oxazolyl group.

For their ease of preparation and level of activity, the most highly preferred compounds are:
5-[4-[3-(2-phenyl-5-methyl-4-oxazolyl)propionyl]benzyl]thiazolidine-2,4-dione;
5-[[5-(1-Hydroxy-3-(2-phenyl-5-methyl-4-oxazolyl)propyl)-2-pyridyl]methyl]thiazolidine-2,4-dione;
5-[[5-(3-(2-Phenyl-5-methyl-4-oxazolyl)propionyl)-2-thienyl]methyl]thiazolidine-2,4-dione; and
5-[[5-(1-Hydroxy-3-(2-phenyl-5-methyl-4-oxazolyl)propyl)-2-thienyl]methylthiazolidione-2,4-dione.

The expression "pharmaceutically-acceptable cationic salts" is intended to define but not limited to such salts as the alkali metal salts, (e.g. sodium and potassium), alkaline earth metal salts (e.g. calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine) diethylamine, piperazine, tromethamine (2-amino-2-hydroxymethyl-1,3-propanediol) and procaine. An especially preferred such salt is the sodium salt.

The expression "pharmaceutically-acceptable acid addition salts" is intended to define but not limited to such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts.

Also embraced by the present invention are pharmaceutical compositions for use in treating a hyperglycemic mammal or a hypercholesterolemic mammal which comprises a blood glucose lowering amount or a blood cholesterol lowering amount of a compound of formula (I) and a pharmaceutically-acceptable carrier. The invention further comprises a method of lowering blood glucose in a hyperglycemic mammal which comprises administering to said mammal a blood glucose lowering effective amount of a compound of formula (I); and a method of lowering blood cholesterol in a hypercholesterolemic mammal which comprises administering to said mammal a blood cholesterol lowering amount of a compound of the formula (I).

DETAILED DESCRIPTION OF THE PRESENT INVENTION

The compounds of the formula (I) of the present invention are readily prepared. Most generally, the compounds of the formula (I) wherein the dotted line represents a bond are prepared by reaction of thiazolidine-2,4-dione with an aldehyde of the formula

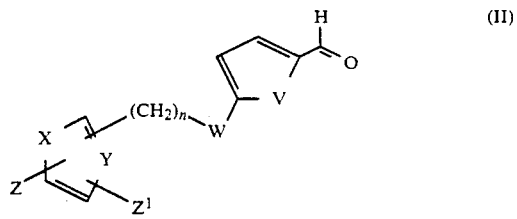

wherein V, W, X, Y, Z, $Z^1$ and n are as defined above. In this step, the reactants are heated in the presence of a mild base to provide the olefin of formula (I) wherein the dotted line represents a bond. Usually a 10–50% molar excess of one of the two reactants is employed, in order to force the reaction to completion within a reasonable period of time. In the present instance, it is generally preferred to use the readily available thiazolidine-2,4-dione in excess. In a preferred method the aldehyde of the formula (II) and the thiazolidinedione are coupled in the presence of a catalytic amount of a secondary amine, preferably pyrrolidine or piperidine, usually about 0.05 to 0.20 molar equivalents, in a reaction-inert solvent such as a lower alkanol (e.g., methanol, ethanol, n-propanol, isopropanol). Temperature is not especially critical, but will generally be above room temperature to effect reasonably rapid completion of the reaction, but below 100° C. to minimize possible side reactions. Reflux temperature of the lower alkanol solvent is particularly convenient. In this method, if desired, when W is CHOH, a protected form of the alcohol (e.g., the dimethyl-t-butylsilyloxy ether derivatives) and when W is CO, a protected form of the ketone (e.g., the cyclic ketals with ethylene glycol) can be used in the present condensation. The protecting group is later removed by conventional means (e.g., by acid catalyzed hydrolysis). Generally, such protecting groups will be used only when they are already in place as part of the strategy of synthesizing the aldehyde of the formula (II).

As used here and elsewhere herein, the expression "reaction inert solvent" refers to a solvent which does not interact with starting materials, reagents, intermediates or products in a manner which adversely affects the yield of the desired product.

In an alternative method the aldehyde of the formula (II) and thiazolidine-2,4-dione are intimately mixed with a molar excess, preferably a 2–4 fold molar excess, of anhydrous sodium acetate and the mixture is heated at a temperature high enough to effect melting, generally about 140°–170° C., at which temperature the reaction is substantially complete in from about 5 to 60 minutes. The desired olefin of formula (I) wherein the dotted line represents a bond is then isolated, for example, by mixing with water and filtration, to obtain the crude product, which is purified, if desired, e.g., by crystallization or by standard chromatographic methods. In this method, when W is CO, it is preferable to minimize the excess of the thiazolidine, and/or to protect the ketone group in the form of a ketal, such as that noted above.

The resulting olefinic products are active hypoglycemic agents, but also serve as intermediates for preparation of the corresponding reduced compounds of formula (I) wherein the dotted line represents no bond. While the reduction of the above olefins can be carried out by employing a number of reducing agents which are known to reduce carbon-to-carbon double bonds, the preferred methods employ hydrogen in the presence of a noble metal catalyst or sodium amalgam in methanol.

When the reduction step is carried out employing hydrogen in the presence of a noble metal catalyst, a convenient method for carrying out this transformation is to stir or shake a solution of the olefinic compound of the formula (I) wherein the dotted line represents a bond in a reaction-inert solvent under an atmosphere of hydrogen, or hydrogen mixed with an inert diluent such as nitrogen, in the presence of a noble metal hydrogenation catalyst. Suitable solvents for this reaction are those which substantially dissolve the starting compound but which do not themselves suffer hydrogenation or hydrogenolysis. Examples of such solvents include ethers such as diethyl ether, tetrahydrofuran, dioxane and 1,2-dimethoxyethane; low molecular weight amides such as N,N-dimethylformamide, N,N-dimethylacetamide and N-methylpyrrolidone; and lower alkyl carboxylic acids such as formic, acetic, propionic and isobutyric acid. An especially preferred such solvent is tetrahydrofuran, particularly when W is CO.

Introduction of the hydrogen gas into the reaction medium is usually accomplished by carrying out the reaction in a sealed vessel, containing the olefinic compound, solvent, catalyst and hydrogen. The pressure inside the reaction vessel can vary from about 1 to about 100 kg/cm². The preferred pressure range, when the atmosphere inside the reaction vessel is substantially pure hydrogen, is from about 2 to about 5 kg/cm². The hydrogenation is generally run at a temperature of from about 0° to about 60° C., and preferably from about 25° to about 50° C. Utilizing the preferred temperature and pressure values, hydrogenation generally takes place in a few hours, e.g., from about 2 hours to about 20 hours. The preferred noble metal catalysts used in this hydrogenation reaction are the type of agents known in the art for this kind of transformation, for example, palladium, platinum and rhodium. A palladium catalyst is preferred because such catalysts are not readily poisoned by sulfur. The catalyst is usually present in an amount from about 0.01 to about 25 weight-percent, and preferably from about 0.1 to about 10 weight-percent, based on the olefinic compound. It is often convenient to suspend the catalyst on an inert support; a particularly convenient catalyst is palladium suspended on an inert support such as carbon.

When in the olefinic compound W is carbonyl (or the protected ketal form thereof) or carbinol (CHOH), more vigorous hydrogenation conditions will generally not only produce the compound of the formula (I) wherein the dotted line no longer represents a bond, but also wherein W is methylene (produced from carbonyl via the carbinol).

When the hydrogenation of the methylene double bond (and when desired, other groups) is substantially complete, the desired product of formula (I) wherein the dotted line is no bond is then isolated by standard methods, e.g., the catalyst is recovered by filtration, the solvent evaporated and the product purified, if desired, by well known methods such as crystallization or by chromatography.

An alternative method for reduction of the olefinic compounds of the formula (I) wherein the dotted line represents a bond is conventional sodium amalgam or metallic magnesium redution in methanol, usually at or about ambient temperature, as exemplified below. When W is CO in the olefin, this method will also generally produce the compound of the formula (I) wherein the dotted line represents no bond and W is CHOH.

The compounds of the formula (I) wherein W is CHOH are also readily prepared by conventional sodium borohydride reduction of the corresponding compound wherein W is CO; and those compounds of the formula (I) wherein W is CO are readily prepared by conventional chromic oxidation, (e.g. chromic acid or pyridinium dichromate) of the corresponding compound wherein W is CHOH. When W is C=NOR, the compounds of the formula (I) are conveniently prepared by conventional reaction of the corresponding carbonyl compound (W=CO) with $H_2NOR$. When W is CH=CH, the compounds of the formula (I) are conveniently prepared by conventional dehydration of a corresponding alcohol compound wherein W=CHOH.

When a saturated compound of the formula (I) wherein the dotted line represents no bond is desired, an alternative synthetic route is to react thiazolidine-2,4-dione with a compound of the formula

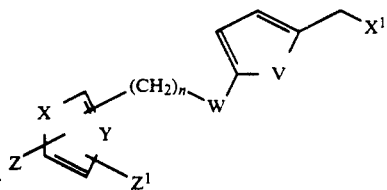

wherein V, W, X, Y, Z, $Z^1$ and n are as defined above, and $X^1$ is a nucleophilic leaving group such as chloride, bromide, iodide or mesylate. These reactants are generally used in substantially equimolar quantities, although 10-25% excess of readily available thiazolidine-2,4-dione is preferred in order to force the reaction to completion within a reasonable period of time. The reaction is carried out in the presence of reaction-inert solvent, such as tetrahydrofuran, with the thiazolidine-2,4-dione prereacted with two molar equivalents of a strong base such as butyl lithium in order to preform the dianion. Salt formation is generally carried out at reduced temperature (e.g. $-50°$ to $-80°$ C.); the reactants mixed at an intermediate temperature, and reaction carried to completion at an elevated temperature (e.g. the reflux temperature of the reaction mixture). It will be evident to those skilled in the art that this method will be preferred only when there are no other reactive groups (e.g., OH, CO) present in the compound of the formula (III). Thus, when W is OH or CO, these groups will generally be in protected form, as discussed above.

The pharmaceutically-acceptable cationic salts of the compounds of the present invention are readily prepared by reacting the acid forms with an appropriate base, usually one equivalent, in a co-solvent. Typical bases are sodium hydroxide, sodium methoxide, sodium ethoxide, sodium hydride, potassium methoxide, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the cation (sodium or potassium ethylhexanoate, magnesium oleate), employing a solvent (e.g., ethyl acetate) from which the desired cationic salt precipitates, or can be otherwise isolated by concentration and/or addition of a non-solvent.

The acid addition salts of the compounds of the present invention are readily prepared by reacting the base forms with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent.

Thiazolidine-2,4-dione is commercially available. The aldehydes of formula (II) are prepared by a variety of conventional methods; for example, by mild oxidation of the corresponding primary alcohol with reagents such as manganese dioxide under conditions known to produce aldehydes from primary alcohols and ketones from secondary alcohols; reaction of the corresponding aralkyl bromides with n-butyl lithium followed by N,N-dimethylformamide at $-80°$ to $-70°$ C., reaction of a suitably 4-substituted benzaldehyde (or corresponding thiophene or pyridine analog) with a suitably substituted heterocyclic derivate so as to form the bridging group:

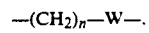—$(CH_2)_n$—W—.

For example, with the aldehyde group usually in protected form or in the form of an aldehyde precursor:

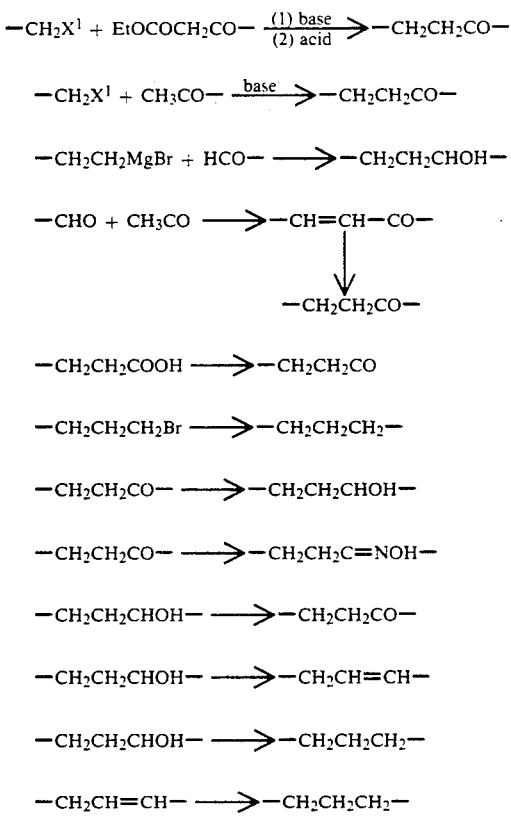

The halides/mesylates of the formula (III) are also available by conventional methods, such as by the action of a suitable reagent (e.g., PBr$_3$, CH$_3$SO$_2$Cl) on the corresponding alcohol, halogenation of a corresponding methyl derivative, and so forth.

It will be further evident to those skilled in the art that the synthesis of a compound of the formula (I) can be varied by the coupling of a precursor aldehyde (or mesylate/halide) with thiazolidine-2,4-dione, with completion of the side chain as a later step by one of the synthetic methods for aldehydes of the formula (II) as illustrated above.

The present compounds of the formula (I) are readily adapted to clinical use as hypoglycemic or hypocholesterolemic agents. The activity required for this former clinical use is defined by the test for hypoglycemic effect in ob/ob mice by the following procedure:

Five to eight week old C57 BL/6J-ob/ob mice (obtained from Jackson Laboratory, Bar Harbor, Me.) were housed five per cage under standard animal care practices. After a one week acclimation period, the animals were weighted and 25 microliters of blood was collected via an ocular bleed prior to any treatment. The blood sample was immediately diluted 1:5 with saline containing 2.5 mg/ml sodium fluoride and 2% sodium heparin, and held on ice for metabolite analysis. Animals were then dosed daily for five days with drug (5–50 mg/kg), a positive control (50 mg/kg) of ciglitazone; U.S. Pat. No. 4,467,902; Sohda et al., Chem. Pharm. Bull., vol. 32, pp. 4460–4465, 1984), or vehicle. All drugs were administered in a vehicle consisting of 0.25% w/v methyl cellulose. On day 5, the animals were weighed again and bled (via the ocular route) for blood metabolite levels. The freshly collected samples were centrifuged for two minutes at 10,000×g at room temperature. The supernatant was analyzed for glucose, for example, by the ABA 200 Bichromatic Analyzer TM, using the A-gent TM glucose UV reagent system* (hexokinase method) using 20, 60 and 100 mg/dl standards. Plasma glucose was then calculated by the equation, Plasma glucose (mg/dl) = Sample value × 5 × 1.67 = 8.35 × Sample value where 5 is the dilution factor and 1.67 is the plasma hematocrit adjustment (assuming the hematocrit is 40%).

TM A registered trademark of Abbot Laboratories, Diagnostics Division, 820 Mission Street, So. Pasadena, CA 91030.
*A modification of the method of Richterich and Dauwalder, Schweizerische Medizinische Wochenschrift, 101, 860 (1971).

The animals dosed with vehicle maintain substantially unchanged hyperglycemic glucose levels (e.g., 250 mg/dl), while positive control animals have depressed glucose levels (e.g., 130 mg/dl). Test compounds are reported in terms of % glucose normalization. For example, a glucose level which is the same as the positive control is reported as 100%.

Studies such as that described below demonstrate that the compounds of formula (I) effect the lowering of serum cholesterol levels in mammals.

Female mice (strain C57Br/cd J), obtained from Jackson Laboratories, Bar Harbor, Me., are used at age 8–12 weeks, following 2–4 weeks acclimation having free access to water and standard laboratory chow. Animals are divided randomly into three groups of 6–7 animals. All three groups are placed on a diet containing 0.75% cholesterol, 31% sucrose, 15.5% starch, 20% casein, 17% cellulose, 4.5% corn oil, 5% coconut oil, 0.25% chloic acid, 4% salts and 2% vitamin; permitted to feed ad lib for 18 days; and dosed daily at 9–11 a.m. for the final 5 days by oral gavage, the control group with 5 ml/kg of vehicle (0.1% aqueous methyl cellulose) and the test groups with the compound under study at doses ranging from 0.1 to 10 mg/kg/day in vehicle. After the fourth day of dosing, the animals are fasted overnight, starting at 5 p.m. The following morning a fifth and final dose of the compound is administered to the test groups and, three hours later, the animals are sacrificed by decapitation. Blood from the body trunk is collected and allowed to clot, and the serum assayed enzymatically, using an Abbott VP automated analyzer, for HDL cholesterol, LDL and VLDL cholesterol, and total cholesterol. Whether judged on the basis LDL+VLDL cholesterol levels, total cholesterol levels or the ratio of LDL+VLDL/HDL, the compounds of this invention generally show favorable result in lowering cholesterol levels.

The present compounds of the formula (I) are clinically administered to mammals, including man, via either the oral or the parenteral route. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 to about 50 mg/kg body weight of the subject per day, preferably about 0.10 to about 10 mg/kg body weight per day administered singly or as a divided dose. However, the optimum dosage for the individual subject being treated will be determined by the person responsible for treatment, generally smaller doses being administered initially and thereafter increments made to determine the most suitable dosage. This will vary according to the particular compound employed and with the subject being treated.

The compound can be used in pharmaceutical preparations containing the compound, or pharmaceutically acceptable acid salt thereof, in combination with a pharmaceutically-acceptable carrier or diluent. Suitable pharmaceutically-acceptable carriers include inert solid fillers or diluents and sterile aqueous or organic solutions. The active compound will be present in such pharmaceutical compositions in amounts sufficient to provide the desired dosage amount in the range described above. Thus, for oral administration the compounds can be combined with a suitable solid or liquid carrier or diluent to form capsules, tablets, powders, syrups, solutions, suspensions and the like. The pharmaceutical compositions may, if desired, contain additional components such as flavorants, sweeteners, excipients and the like. For parenteral administration the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts of the compounds. The injectable solutions prepared in this manner can then be administered intravenously, intraperitoneally, subcutaneously, or intramuscularly, with intramuscular administration being preferred in man.

The present invention is illustrated by the following Examples. However, it should be understood that the invention is not limited to the specific details of these examples. Nomenclature used herein is based on Rigaudy and Klesney, IUPAC Nomenclature of Organic Chemistry, 1979 Ed., Pergammon Press, New York 1979. The abbreviations THF, DMF and DMSO refer to tetrahydrofuran, dimethylformamide and dimethylsulfoxide respectively.

EXAMPLE 1

5-[4-(3-(5-Methyl-2-phenyl-4-oxazolyl)propionyl)-phenylmethylene]thiazolidine-2,4-dione 4-[3-(5-Methyl-2-phenyl-4-oxazolyl)propionyl]benzaldehyde, the title product of Preparation 4, (16 g, 0.05 mol), thiazolidine-2,4-dione (11.7 g, 0.10 mol and piperidine (0.85 g, 0.01 mol) were combined in 300 mL absolute ethanol, and the mixture refluxed for 24 hours, cooled to 0° C., diluted slowly with 600 mL of ether and, after stirring for 1 hour at 0° C., crude product recovered by filtration. The crude product was triturated with 150 mL of warm acetic acid (40°-50° C.). The resulting slurry was cooled to room temperature, diluted with 300 mL of ether, and 14.2 g (71%) of purified title product recovered by filtration; mp 224°-225° C.

By the same method, 4-[3-(5-methyl-2-(4-methylphenyl)-4-oxazolyl)propionyl]benzaldehyde (1.55 g, 4.65 mmols); 4-[3-[5-methyl-2-(2-naphthyl)-4-oxazolyl]-propionyl]benzaldehyde (2.20 g, 6 mmole); 4-[3-(5-methyl-2-[4-(trifluoromethyl)phenyl)-4-oxazolyl)propionyl]benzaldehyde (780 mg, 2.01 mmol); 4-[3-(5-methyl-2-(5-methyl-2-furyl)-4-oxazolyl)propionyl]benzaldehyde (470 mg, 1.45 mmol); 4-[3-(2-(4-methylphenyl)-4-oxazolyl)propionyl]benzaldehyde (3.60 g, 11.3 mmol); and 4-[3-(1,4-dimethyl-2-phenyl-5-imidazolyl)propionyl]benzaldehyde (800 mg, 2.4 mmol) were reacted with thiazolidine-2,4-dione to yield, respectively;

5-[4-[3-(5-methyl-2-(4-methylphenyl)-4-oxazolyl)propionyl]phenylmethylene]thiazolidine-2,4-dione, 560 mg, mp 250°-251° C.

5-[4-[3-(5-methyl-2-(2-naphthyl)-4-oxazolyl)propionyl]-phenylmethylene]thiazolidine-2,4-dione, 1.0 g, mp 221°-222° C.

5-[4-[3-(5-methyl-2-(4-(trifluoromethyl)phenyl)-4-oxazolyl)propionyl]phenylmethylene]thiazolidine-2,4-dione, 300 mg, mp 244°-245° C.;

5-[4-[3-(5-methyl-2-(5-methyl-2-furyl)-4-oxazolyl)propionyl]phenylmethylene]thiazolidine-2,4-dione, 310 mg, mp 236°-238° C.

5-[4-[3-(2-(4-methylphenyl)-4-oxazolyl)propionyl]-phenylmethylene]thiazolidine-2,4-dione, 1.30 g, mp 220°-223° C.; and 5-[4-[3-(1,4-dimethyl-2-phenyl-5-imidazolyl)propionyl]-phenylmethylene]thiazolidine-2,4-dione, 670 mg.

By substituting a molar equivalent of 4-[3-(1-methyl-2-pyrrolyl)propionyl]benzaldehyde or 4-[3-(2-imidazolyl)propionyl]benzaldehyde for the present aldehyde, this method is used to prepare 5-[4-(3-(1-methyl-2-pyrrolyl)propionyl)phenylmethylene]thiazolidine-2,4-dione and 5-[4-(3-(2-imidazolyl)propionyl)phenylmethylene]thiazolidine-2,4-dione.

EXAMPLES 2-8

5-[4-(3-(Substituted)propionyl)phenylmethylene]-thiazolidine-2,4-diones

Substituting a molar equivalent of the appropriately substituted benzaldehyde of Preparations 5-11 for the substituted benzaldehyde of the preceding Example, thiazolidine-2,4-dione was converted to the following additional products:

| No | Substituent | Yield (%) | mp (°C.) |
|---|---|---|---|
| 2 | 2-Phenyl-4-oxazolyl | 55 | 228-230 |
| 3 | 2-(4-Methoxyphenyl)-5-methyl-4-oxazolyl | 76 | 221-222 |
| 4 | 2-(2-Thienyl)-5-methyl-4-oxazolyl | 62 | 237-238 |
| 5 | 2-(2-Furyl)-5-methyl-4-oxazolyl | 75 | 236-237 |
| 6 | 2-Cyclohexyl-5-methyl-4-oxazolyl | 46 | gum[a] |
| 7 | 2-Phenyl-4-thiazolyl | 55 | 205-207 |
| 8 | 2-Phenyl-4-methyl-5-thiazolyl | 35 | 208-210 |

[a]¹H-NMR (DMSO-d₆) delta (ppm) 1.2-2.0 (m, 10), 2.2 (s, 3H), 2.7 (m, 3H), 3.3 (t, 2H), 7.7 (d, 2H), 7.8 (s, 1H), 8.1 (d, 2H).

EXAMPLE 9

5-[4-(3-(5-Methyl-2-phenyl-4-oxazolyl)propionyl)benzyl]thiazolidine-2,4-dione

Title product of Example 1 (14.2 g) was hydrogenated in 800 ml of THF in the presence of 10 g of Pd/C in a Paar shaker at 50 psig and room temperature for 24 hours. Catalyst was recovered by filtration over diatomaceous earth with THF wash. The combined filtrate and wash liquor was stripped to a gum, which was crystallized by trituration with 250 ml 1:1 hexane:ethyl acetate to yield 11.4 g of recrystallized title product; mp 145°-146° C.

Anal. Calcd. for $C_{23}H_{18}N_2O_4S$: C, 65.70; H, 4.79; N, 6.66. Found: C, 65.67; H, 4.76; N, 6.59.

By the same method, the additional products of Example 1 were converted to:

5-[4-[3-(5-methyl-2-(4-methylphenyl)-4-oxazolyl)propionyl]benzyl]thiazolidine-2,4-dione, 150 mg from 520 mg, mp 240°–242° C.

5-[4-[3-(5-methyl-2-(2-naphthyl)-4-oxazolyl)propionyl]benzyl]thiazolidine-2,4-dione, 635 mg from 900 mg, mp 188°–189° C.

5-[4-[3-(5-methyl-2-(4-(trifluoromethyl)phenyl)-4-oxazolyl)propionyl]benzyl]thiazolidine-2,4-dione, 95 mg from 250 mg, mp 150°–153° C.; and 5-[4-[3-(5-methyl-2-(5-methyl-2-furyl)-4-oxazolyl)propionyl]benzyl]thiazolidine-2,4-dione, 180 mg of an oil from 250 mg, converted to sodium salt by the action of $NaOCH_3$ in methanol with stripping and repulp of the residue in ethyl acetate, 120 mg, mp 225° C. (dec.); and 5-[4-[3-(2-(4-methylphenyl)-4-oxazolyl)propionyl]benzyl]thiazolidine-2,4-dione, 301 mg from 1.12 g, mp 143°–144° C.

By the same method, the additional products of Example 1 are converted to 5-[4-(3-(1-methyl-2-pyrrolyl)-propionyl)benzyl]thiazolidine-2,4-dione and 5-[4-(3-(2-imidazolyl)propionyl)benzyl]thiazolidine-2,4-dione; and 5-[[5-(1-hydroxy-3-(2-phenyl-5-methyl-4-oxazolyl)-propyl)-1-benzyl-2-pyrrolyl]methylene]thiazolidine-2,4-dione of Example 23 is converted to 5-[[5-(1-hydroxy-3-(2-phenyl-5-methyl-4-oxazolyl)propyl)-2-pyrrolyl]methyl]thiazolidine-2,4-dione.

EXAMPLE 10–16

5-[4-(3-(Substituted)propionyl)benzyl]thiazolidine-2,4-diones

By the method of the preceding Example, the products of Examples 2–8 were converted to the following additional products:

| No | Substituent | Yield (%) | mp (°C.) |
|---|---|---|---|
| 10 | 2-Phenyl-4-oxazolyl | 80 | 151–155 |
| 11 | 2-(4-Methoxyphenyl)-5-methyl-4-oxazolyl | 63 | 173–174 |
| 12 | 2-(2-Thienyl)-5-methyl-4-oxazolyl | 82 | 157–158 |
| 13 | 2-(2-Furyl)-5-methyl-4-oxazolyl | 88 | 155–156 |
| 14 | 2-Cyclohexyl-5-methyl-4-oxazolyl | 50 | 190–195[a] |
| 15 | 2-Phenyl-4-thiazolyl | 60 | 139–142 |
| 16 | 2-Phenyl-4-methyl-5-thiazolyl | 82 | 118–120 |

[a]As the sodium salt, obtained according to the method of Example 23, below.

EXAMPLE 17

5-[4-(3-(2-phenyl-5-methyl-4-oxazolyl)-1-hydroxypropyl)benzyl]thiazolidine-2,4-dione The title product of Example 9 (0.70 g) was suspended in 50 ml of isopropanol at room temperature. $NaBH_4$ (0.15 g) was added and the mixture stirred for 2 hours, concentrated in vacuo to low volume, diluted with 50 ml of water and extracted 2×200 mL ethyl acetate. The organic layers were combined, washed with brine, dried ($MgSO_4$), stripped in vacuo and the residue chromatographed using 1:1 ethyl acetate:hexane-1% acetic acid to yield 0.32 g of present title product; mp 50°–55° C.; tlc Rf 0.40 (1:1 hexane:ethyl acetate-2.5% acetic acid), 0.28 (2:1 $CH_2Cl_2$:ether).

EXAMPLE 18

5-[[5-(3-(2-Phenyl-5-methyl-4oxazolyl)propionyl)-2-pyridyl]methylene]thiazolidine-2,4-dione To title product of Preparation 17 (0.42 g, 1.35 mmol) in 2 mL ethanol was added thiazolidine-2,4-dione (0.315 g, 2.7 mmol) and 0.03 mL of piperidine. The mixture was refluxed for 18 hours, cooled and 0.14 g (25%) of present title product recovered by filtration; mp 228°–230° C.

EXAMPLE 19

5-[[5-(3-(2-Phenyl-5-methyl-4-oxazolyl)-1-hydroxypropyl)-2-pyridyl]methyl]thiazolidine 2,4-dione To title product of the preceding Example (0.14 g) in 20 mL $CH_3OH$ was added 1% Na/Hg amalgam (10 g) and the mixture stirred for 3 hours. The organic phase was decanted and stripped of solvent in vacuo and the residue taken up in 10 mL water, the pH adjusted to 4.5 with 1N HCl, and extracted 3×10 mL $CH_2Cl_2$. The organic layers were combined, dried ($MgSO_4$), stripped in vacuo and the residue (130 mg) taken up in 3:17 $CH_3OH$:$CHCl_3$ and filtered through a plug of silica gel with elution by the same solvent system to yield 92 mg of present title product as a foam.

$^1$H-NMR (CDCl$_3$) delta (ppm) 8.53 (d, J=1.8 Hz, 1H), 7.95 (m, 2H), 7.74 (dd, J=2.2, 8.1 Hz, 1H), 7.42 (m, 3H), 7.18 (d, J=8.0 Hz, 1H), 4.91 (dd, J=3.9, 8.3 Hz, 1H), 4.83 (ddd, J=1.4, 3.8, 10.2 Hz, 1H), 3.77 (ddd, J=3.5, 3.5, 16 Hz, 1H), 3.34 (ddd, J=1.6, 9.8, 16 Hz, 1H), 2.69 (m, 2H), 2.33 (s, 3H), 2.08 (m, 2H).

By the same method, 5-[4-[3-(1,4-dimethyl-2-phenyl-5-imidazolyl)propionyl]phenylmethylene]thiazolidine-2,4-dione (480 mg) was converted to 5-[4-[1-hydroxy-3-(1,4-dimethyl-2-phenyl-5-imidazolyl)propyl]benzyl]-thiazolidine-2,4-dione, 166 mg, $^1$H-NMR includes 7.6-7.1 (m, 9H), 5.30 (br s, 1H), 4.54 (t, 1H), 4.15 (dd, 1H), 3.51 (s, 3H), 3.40 (m, 2H), 2.55 (m, 2H), 2.08 (s, 3H), 1.80 (m, 2H).

EXAMPLE 20

5-[[5-(1-(Dimethyl-t-butylsilyoxy)-3-(2-phenyl-5-methyl-4-oxazolyl)propyl)-2-thienyl]methylene]thiazolidine-2,4-dione Title product of Preparation 23 (1.81 g, 4.1 mmol), thiazolidine-2,4-dione (0.96 g, 8.2 mmol) and piperidine (0.1 mL, 0.82 mmol) were combined in 40 mL ethanol and heated at reflux for 4 hours. The solvent was stripped in vacuo and the residue taken up in 40 mL ethyl acetate, washed 2×25 mL 0.5N HCl and 3×25 mL water, dried ($MgSO_4$) and stripped to yield 2.17 g of present title product as an oil; tlc Rf 0.35 ($CHCl_3$).

By the same method, the following 5-[1-[dimethyl-t-butylsilyloxy]-3-[substituted-4-oxazolyl]propyl]thiophene-2-carbaldehydes:

| Oxazole Substituent(s) | Amount |
|---|---|
| 2-(4-chlorophenyl)-5-methyl | 2.80 g, 6.25 mmol |
| 2-(4-(trifluromethyl)phenyl | 650 mg, 1.3 mmol |
| 2-(4-(trifluoromethyl)phenyl)-5-methyl | 6.83 g, 13.4 mmol |
| 2-(4-methylphenyl)-5-methyl | 117.7 g, 0.258 mol | were converted to the corresponding 5-[[5-(1-(dimethyl-t-butylsilyloxy)-3-(substituted-4-oxazolyl)propyl)-2-thienyl]methylene]thiazolidine-2,4-diones, as follows:

| Oxazole Substituent(s) | Amount | tlc Rf |
| --- | --- | --- |
| 2-(4-chlorophenyl)-5-methyl | 3.46 g | 0.45 (1:3 ethyl acetate:hexane) |
| 2-(4-(trifluoromethyl)phenyl | 760 mg | 0.35 (1:4 ethyl acetate:hexane) |
| 2-(4-(trifluoromethyl)phenyl 5-methyl | 8.10 g | 0.30 (1:4 ethyl acetate:hexane) |
| 2-(4-(methylphenyl)-5-methyl | 157.0 g. | 0.30 (1:9 ethyl acetate:hexane) |

By the same method, the other products of Preparation 23 were converted to 5-[[5-(1-dimethyl-t-butylsilyloxy)-3-(2-phenyl-5-methyl-4-oxazolyl)propyl)-1-(methyl- or benzyl)]methylene]thiazolidine-2,4-dione.

EXAMPLE 21

5-[[5-(1-(Dimethyl-t-butylsilyloxy)-3-(2-phenyl-5-methyl-4-oxazolyl)propyl)-2-thienyl]methyl]thiazolidine-2,4-dione Title product of the preceding Example (2.17 g, 4.0 mmol) and 1.2% Na/Hg amalgam (40 g) were combined with methanol (100 mL) and the mixture stirred for 3.5 hours at room temperature. The organic phase was decanted and stripped in vacuo to an oil, which was suspended in 50 mL water, acidified to pH 2 with 6N HCl and extracted 3×50 mL $CH_2Cl_2$. The organic layers were combined, dried ($MgSO_4$) and stripped to yield 1.56 g of title product as an oil; tlc Rf 0.60 (1:19 $CH_3OH:CHCl_3$).

With partial loss of aromatic Cl, and concurrent conversion of $CF_3$ groups to $CH_3$ groups, other products of the preceding Example were converted to 5-[[5-(1-(dimethyl-t-butylsilyloxy)-3-(substituted-4-oxazolyl)-propyl)-2-thienyl]methyl]thiazolidine-2,4-diones as follows:

| Oxazole Substituent(s) | |
| --- | --- |
| 2-(4-chlorophenyl-5-methyl and 2-phenyl-5-methyl (1:1) | 2.80 g from 3.41 g, oil |
| 2-(4-methylphenyl) | 360 mg from 755 mg, oil |
| 2-(4-methylphenyl-5-methyl | 4.76 g from 7.38 g of 4-$CF_3$ analog: 152.8 g from 156.0 g of 4-$CH_3$ analog; oil |

EXAMPLE 22

5-[[5-(1-Hydroxy-3-(2-phenyl-5-methyl-4-thiazolyl)-propyl)-2-thienyl]methyl]thiazolidine-2,4-dione Title product of the preceding Example (1.28 g), 6N HCl (50 mL) and THF (50 mL) were combined and stirred for 1 hour at room temperature. The pH was adjusted to 3 with saturated $NaHCO_3$ and the mixture extracted 3×75 mL ethyl acetate. The combined organic layers were washed 1×75 mL water, dried ($MgSO_4$), stripped in vacuo and the residue chromatographed on a 4 mm plate of silica gel using 1:9 ethyl acetate:hexane as eluant, eluting product at Rf 0.1, to yield 0.51 g of present title product as an oil; tlc Rf 0.2 (1:19 $CH_3OH:CHCl_3$).

By the same method, but utilizing 2N HCl in place of 6N HCl, the other products of the preceding Example were converted to corresponding 5-[[5-(1-hydroxy-3-(substituted-4-oxazolyl)propyl)-2-thienyl]methyl]-thiazolidine-2,4-diones as follows:

| Oxazole Substituent(s) | Amount |
| --- | --- |
| 2-(4-chlorophenyl)-5-methyl and 2-phenyl-5-methyl (1:1) | 1.36 g from 2.79 g[a] |
| 2-(4-methylphenyl) | 260 mg from 360 mg[b] |
| 2-(4-methylphenyl)-5-methyl | 3.70 g from 4.74 g[c] |

[a] tlc Rf 0.55 (1:1 ethyl acetate:hexane)
[b] tlc Rf 0.25 (1:3 ethyl acetate:hexane)
[c] tlc Rf 0.35 (1:9 ethyl acetate:hexane)

By the same method the appropriate dimethyl-t-butylsilyl ether compound of Example 19 (600 mg, 0.99 mmol) was converted to 5-[[5-(1-hydroxy-3-(5-methyl-2-(4-(trifluoromethyl)phenyl)-4-oxazolyl)propyl]-2-thienyl]methylene]thiazolidine-2,4-dione, 250 mg, tlc Rf 0.2 (1:3 ethyl acetate:hexane).

The latter case was repeated using 6N HCl and 152.7 g (0.274 mol) of 5-[[5-(1-(dimethyl-t-butylsilyloxy)-3-(2-(4-methylphenyl)-5-methyl-4-oxazolyl)propyl)-2-thienyl]methyl]thiazolidine-2,4-dione of the preceding Example, adjusting the pH to 5 with $NaHCO_3$ and chromatographing the crude product (115 g of oil) on silica gel gradiently eluting with hexane to 3:7 ethyl acetate:hexane. In this case, the principal product isolated was 41.7 g of dehydrated product, viz., 5-[[5-(3-(2-(4-methylphenyl)-5-methyl-4-oxazolyl)-1-propenyl)-2-thienyl]methyl]oxazolidine-2,4-dione as an oil. The latter (31.1 g) was converted to 23 g of crude sodium salt according to the method of Example 27 below and purified by trituration with 1:1 ether:ethyl acetate to yield 9.13 g of purified sodium salt; mp 245°–250° C.

Anal. Calcd. for $C_{22}H_{19}N_2S_2O_3Na$; 0.5 $H_2O$: C, 58.00; H, 4.43; N, 6.15. Found: C, 57.71; H, 4.18; N, 6.22.

By the method of Examples 21 and 22, the various other products of Example 20 were converted to 5-[[5-(1-hydroxy-3-(2-phenyl-5-methyl-4-oxazolyl)propyl)-2-thienyl]methylene]thiazolidine-2,4-dione, 5-[[5-(1-hydroxy-3-(2-phenyl-5-methyl-4-oxazolyl)propyl)-1-methyl-2-pyrrolyl]methylene]thiazolidine-2,4-dione and 5-[[5-(1-hydroxy-3-(2-phenyl-5-methyl-4-oxazolyl)-propyl)-1-benzyl-2-pyrrolyl]methylene]thiazolidine-2,4-dione.

EXAMPLE 23

Sodium Salt of 5-[[5-(1-Hydroxy-3-(2-phenyl-5-methyl-4-thiazolyl)-propyl)-2-thienyl]methyl]thiazolidine-2,4-dione Title product of the preceding Example (169 mg, 0.40 mmol) was dissolved in 5 mL of ether. Sodium 2-ethylhexanoate (69 mg, 0.41 mmol) was added. The resulting slurry was stirred as sufficient ethyl acetate (5 mL) was added to achieved dissolution. After stirring overnight at room temperature, 63 mg of present title product was recovered by filtration; mp 206°–210° C.

EXAMPLE 24

5-[[5-(3-(2-Phenyl-5-methyl-4-thiazolyl)propionyl)-thienyl]methyl]thiazolidine-2,4-dione To title product of Example 22 (0.16 g, 0.37 mmol) dissolved in $CH_2Cl_2$ (10 mL) was added pyridinium dichromate (281 mg, 0.75 mmol). After stirring overnight, diatomaceous earth (3 g) and ether (40 mL) were added, and the mixture was filtered over a pad of diatomaceous earth with ether wash. The combined filtrate and wash was stripped in vacuo and the residue chromatographed on a 2 mm silica gel plate using gradient elution with from 1:19 to 1:1 ethyl acetate:hexane, the fourth band to elute being the desired product. Present title product (110 mg) was recovered as a white solid, recrystallized from ethyl acetate/cyclohexane to yield 88 mg of purified title product; mp 164°-166° C.

Anal. Calcd. for $C_{21}H_{18}N_2O_4S_2$: C, 59.14; H, 4.25; N, 6.57. Found: C, 58.89; H, 4.23; N, 6.30.

By the same method, the other products of Example 22 were converted to the corresponding 5-[[5-(3-(substituted-4-oxazolyl)propionyl)thienyl]methyl]thiazolidine-2,4-diones as follows:

| Oxazole Substituent(s) | Amount | mp (°C.) |
|---|---|---|
| 2-(4-chlorophenyl)-5-methyl and 2-phenyl-5-methyl (1:1) | 550 mg from 1.36 g | 147-149 |
| 2-(4-methylphenyl) | 40 mg from 80 mg | 151-153 |
| 2-(4-methylphenyl)-5-methyl | 1.36 g from 1.46 g | 158-160 | and 5-[[5-(3-(5-methyl-2-(4-(trifluoromethyl)phenyl)-4-oxazolyl)propionyl]-2-thienyl]methylene]thiazolidine-2,4-dione, 80 mg from 240 mg, mp 171°-175° C.

EXAMPLE 25

Potassium Salt of 5-[4-(3-(2-Furyl)-2-propenoyl)benzyl]thiazolidine-2,4-dione

Potassium t-butoxide (123 mg, 1.1 mmol) was dissolved with stirring in 10 mL ethanol. 5-(4-Acetylbenzyl)thiazolidine-2,4-dione (249 mg, 1.0 mmol) was added and the mixture stirred vigorously for 15 minutes, following which 2-furfural (106 mg, 1.1 mmol) was added and the resulting suspension heated at reflux. After 10 minutes, the mixture was a clear solution. After 20 minutes, product began to precipitate. After 1 hour of reflux, the mixture was cooled to room temperature and 182 mg of title product recovered by filtration with ether wash; mp 270°-275° C. (dec); tlc Rf 0.5 (1:1 ethyl acetate:hexane/5% acetic acid).

EXAMPLE 26

5-[4-(3-(2-Furyl)propionyl)benzyl]thiazolidine-2,4-dione

Title product of the preceding Example (420 mg) and 10% Pd/C (420 mg) were combined in 40 mL methanol and the mixture hydrogenated in a Paar shaker at 50 psig for 4 hours, by which time tlc indicated consumption of starting material with conversion to the desired product (Rf 0.8 in the tlc system of the preceding Example). The catalyst was recovered by filtration with CH$_2$Cl$_2$ wash. The combined filtrate and wash was stripped of solvent and the residue chromatographed on 30 g silica gel using 1:1 ethyl acetate:hexane/2.5% acetic acid as eluant monitoring by tlc, to yield 127 mg of present title product as a gum, having tlc properties as indicated above.

EXAMPLE 27

Sodium Salt of 5-[4-(3-(2-Furyl)propionyl)benzyl]thiazolidine-2,4-dione

Title product of the preceding Example (127 mg, 0.47 mmol) was dissolved with warming in 2 mL ethyl acetate. Sodium 2-ethyl hexanoate (79 mg, 0.47 mmol) separately dissolved in 2 mL ethyl acetate was added. Present title product (90 mg) separated as a white solid and was recovered by filtration with ether wash; mp 265°-270° C. (dec).

EXAMPLE 28

5-[4-(3-(1-Hydroxy-3-(2-pyridyl)propyl)benzyl]thiazolidine-2,4-dione

A mixture of 4-[3-(2-pyridyl)propionyl]benzaldehyde (345 mg, 1.44 mmol), thiazolidine-2,4-dione (210 mg, 1.8 mmol) and sodium acetate (300 mg, 3.6 mmol) was heated to 140° C. for 30 minutes. The result mass was cooled, broken up and triturated with water, and intermediate 5-[4-(3-(2-pyridyl)propionyl)benzyl]thiazolidine-2,4-dione recovered by filtration. This intermediate was dissolved in methanol (15 mL) and treated with 3% sodium amalgam (3 g) and the mixture was stirred overnight. The solution was decanted, diluted with water (20 mL) and neutralized with 1N HCl, then extracted with ethyl acetate (3×15 mL). The combined extracts were washed with brine (15 mL), dried over magnesium sulfate and concentrated in vacuo. The product was purified by flash-chromatography (dichloromethane:methanol, 15:1) and obtained as a yellow solid (60 mg, 12%).

HRMS Calcd. for $C_{18}H_{19}N_2O_3S$: 343.1116. Found: 343.1055.

EXAMPLE 29

5-[4-[3-(5-Methyl-2-phenyl-4-oxazolyl)-1-propenyl]benzyl]thiazolidine-2,4-dione

A solution of the title product of Example 17 (0.25 g) in 3 mL of F$_3$CCOOH was heated at reflux for 5 hours, cooled, stripped and the residue flash chromatographed on silica gel using CH$_2$Cl$_2$:CH$_3$OH 30:1 as eluant to yield 225 mg (94%) of present title product; mp 55°-57° C.

EXAMPLE 30

5-[4-[3-(5-Methyl-2-phenyl-4-oxazolyl)propyl]benzyl]thiazolidine-2,4-dione

Title product of the preceding Example (225 mg) in 25 mL of ethyl acetate was hydrogenated over 225 mg of Pd/C for 18 hours. The catalyst was recovered by filtration over diatomaceous earth, the filtrate stripped, and the residue flash chromatographed on silica gel using 3:2 hexane:ethyl acetate as eluant to yield 130 mg (57%) of present title product as an oil; $^1$H-NMR (300 MHz, CDCl$_3$) delta (ppm) 1.96 (quint, J=7.5 Hz, 2H), 2.26 (s, 3H), 2.49 (t, J=7.6 Hz, 2H), 2.63 (t, J=7.7 Hz, 2H), 3.07 (dd, J=14.1, 9.7 Hz, 1H), 3.47 (dd, J=14.1, 4.0 Hz, 1H), 4.47 (dd, J=9.9, 4.0 Hz, 1H), 7.11 (AB, J=8.5 Hz, 2H), 7.15 (AB, J=8.6 Hz, 2H), 7.37-7.42 (m, 3H), 7.94-7.97 (m, 2H), 8.64 (br, 1H).

EXAMPLE 31

5-[4-[3-(5-Methyl-2-phenyl-4-oxazolyl)-1-oximinopropyl)benzyl]thiazolidine-2,4-dione Title product of Example 9 (0.10 g, 0.238 mmol), hydroxylamine hydrochloride (0.041 g, 0.595 mmol) and 2 mL of pyridine were combined in 3 mL of ethanol and the mixture stirred 18 hours at room temperature, then stripped of solvent and the residue taken up in 7.5 mL ethyl acetate, washed with 5 mL of cold 18% HCl and then 5 mL brine, dried (MgSO$_4$) and stripped to yield 0.086 g of present title product as a white solid; mp 202°-205° C.; tlc Rf 0.53 (1:1 hexane:ethyl acetate).

EXAMPLE 32

5-[4-(3-(5-Methyl-2-phenyl-4-oxazolyl)-1-methoxyimino)propyl)benzyl]thiazolidine-2,4-dione By the method of the preceding Example, substituting 0.05 g of methoxylamine hydrochloride for the hydroxylamine hydrochloride, the title product of Example 9 (0.100 g, 0.238 mmol) was converted to 0.090 g of present title product, which was further purified by recrystallized from ethyl acetate and hexane; mp 138°–140° C.

PREPARATION 1

1-[4-(Diethoxymethyl)phenyl]ethanol 4-(Diethoxymethyl)benzaldehyde (104 g, 0.5 mol) was dissolved in 300 ml of ether and the resulting solution cooled to −75° C. in an acetone-dry ice bath. With vigorous stirring, methyllithium (390 mL of 1.4M in ether, 0.55 mol) was added at a rate which maintained the temperature at less than −60° C. The reaction mixture was allowed to warm to room temperature, stirred for two hours at that temperature, poured into 500 mL of ice and water, stirred 10 minutes and the layers separated. The aqueous layer was extracted with 500 mL ether. The organic layers were combined, washed with 500 mL each of $H_2O$ and then brine dried ($MgSO_4$) and stripped in vacuo to yield 110–111.5 (98–100%) of present title product as a viscous, light yellow oil.

PREPARATION 2

4-(Diethoxymethyl)acetophenone

Title product of the preceding Example (223 g, 1.0 mol) and $MnO_2$ (480 g, 5.5 mol) were combined in 2.5 L of toluene and, with vigorous stirring, the resulting dark suspension refluxed for 18 hours, cooled to room temperature, and clarified by filtration over diatomaceous earth with ethyl acetate wash. The combined filtrate and wash liquor was stripped in vacuo to yield 196 g crude title product as a light yellow syrup. The latter was distilled to yield 134 g (60%) of present, purified title product, bp 113°–115° C. at 0.2–0.7 mm (pot temperature 155°–157° C.).

PREPARATION 3

Ethyl 2-[4-(Diethoxymethyl)benzoyl]acetate

Ether (400 mL) was cooled to 0°–5° C. With vigorous stirring, NaH (97%, 32.4 g, 1.35 mol) was added followed immediately by diethyl carbonate (95.6 g, 0.81 mol). After stirring for 25 minutes at room temperature, a mixture of title product of the preceding Preparation (120 g, 0.54 mol) and 1 mL of absolute ethanol in 300 mL of ether was added over a 25 minute period with continued vigorous stirring at room temperature. The reaction mixture was slowly heated to reflux and refluxed for 6 hours. The reaction mixture was cooled to room temperature and then slowly poured into a mixture of 500 mL 10% HCl and 500 mL ether previously chilled to 0° C. The aqueous layer was separated and extracted with 500 mL of fresh ether. The organic layers were combined, washed with 500 mL water and then 500 mL brine, dried ($MgSO_4$) and stripped in vacuo to a yield 158 g (99%) of present title product as a viscous oil.

PREPARATION 4

4-[3-(5-Methyl-2-phenyl-4-oxazolyl)propionyl]benzaldehyde

Sodium hydride (3.4 g, 0.14 mol) was combined with 250 ml THF and cooled to 0° C. With stirring, the title product of the preceding Preparation (41.5 g, 0.14 mol) in 250 mL of THF was added portionwise over 0.5 hour, maintaining the temperature below 25° C. After stirring for an additional 0.5 hour at room temperature, (5-methyl-2-phenyl-4-oxazolyl)methyl chloride (25.8 g, 0.125 mol) was added and the mixture heated at reflux for 48 hours, cooled and stripped in vacuo to yield the expected intermediate product. The entire batch of intermediate product was taken up in a mixture of 360 mL of acetic acid and 90 mL concentrated HCl, heated at reflux for 5 hours, cooled to room temperature, diluted with 600 mL water, and extracted 2×1 L 1:1 ethyl acetate:ether. The organic layers were combined, washed with 1 L each of water and brine, dried ($MgSO_4$), stripped of solvent in vacuo and the residue flash chromatographed on silica gel using 1:19 ether:$CHCl_3$ as eluant to yield 34 g (85%) of present title product as an oil which solidified on standing; mp 76°–80° C.

PREPARATIONS 5-11

4-[3-(Substituted)propionyl]benzaldehydes

By the method of the preceding Example, substituting a molar equivalent of the appropriately substituted (oxazolyl)methyl or (thiazolyl)methyl chloride for (5-methyl-2-phenyl-4-oxazolyl)methyl chloride, the title product of Preparation 3 was converted to the following additional products:

| No | Substituent | Yield (%) | mp (°C.) |
|---|---|---|---|
| 5 | 2-Phenyl-4-oxazolyl | 65 | oil |
| 6 | 2-(4-Methoxyphenyl)-5-methyl-4-oxazolyl | 38 | 78–80 |
| 7 | 2-(2-Thienyl)-5-methyl-4-oxazolyl | 70 | gum |
| 8 | 2-(2-Furyl)-5-methyl-4-oxazolyl | 35 | 98–100 |
| 9 | 2-Cyclohexyl-5-methyl-4-oxazolyl | 29 | gum |
| 10 | 2-Phenyl-4-thiazolyl | 41 | 101–104 |
| 11 | 2-Phenyl-4-methyl-5-thiazolyl | 29 | gum |

PREPARATION 12

Methyl 2-(Dimethyl-t-butylsilyloxymethyl)pyridine-5-carboxylate

To methyl 2-(hydroxymethyl)pyridine-5-carboxylate (0.77 g, 4.61 mmol) in 10 mL DMF was added dimethyl-t-butylsilyl chloride (0.77 g, 1.1 equivalents) and imidazole (0.47 g, 1.5 equivalents). After 1 hour, the reaction mixture was poured into 30 mL water and extracted 3×20 mL ether. The organic layers were combined, washed 2×20 mL water, dried ($MgSO_4$) and stripped in vacuo to yield 1.32 g (100%) of present title product.

PREPARATION 13 t-Butyl 3-[2-(Dimethyl-t-butylsilyloxymethyl)-5-pyridyl]-3-oxopropionate n-Butyllithium (4.75 mL of 2.0M in hexane, 9.5 mmol) and diisopropylamine (1.36 mL, 9.7 mmol) were combined in 10 mL THF at −78° C., warmed to room temperature and recooled to −78° C., at which time t-butyl acetate (1.28 mL, 9.5 mmol) was added and the mixture stirred at −78° C. for 15 minutes to form the enolic lithium salt of the t-butyl acetate. The entire product of the preceding Preparation (4.61 mmol) in 5 ml of THF was added to the cold solution of the enolic salt. After warming and stirring for 2 hours at room temperature, the reaction mixture was quenched into 50 mL water and extracted with 4×20 mL ether. The organic layers were combined, dried (MgSO$_4$), stripped in vacuo, and the residue chromatographed on a 4 mm plate of silica gel with 3:7 ether:hexane as eluant to yield 0.94 g (56%) of present title product.

PREPARATION 14

2-[(Dimethyl-t-butylsilyloxy)methyl]-5-[3-(2-phenyl-5-methyl-4-oxazolyl)-2-(t-butoxycarbonyl)propionyl]-pyridine Sodium hydride (107 mg of 60% in oil, 2.68 mmol) was washed 3×3 mL hexane and then combined with 5 mL of dry DMF. A solution of the title product of the preceding Preparation (0.89 g, 2.44 mmol) in 4 mL of DMF was added over 2 minutes and the mixture stirred at room temperature for 15 minutes and at 50° C. for 5 minutes to form the intermediate beta-keto ester anion. At 50° C., (2-phenyl-5-methyl-2-oxazolyl)methyl chloride (0.506 g., 2.44 mmol) was added and the mixture stirred at 70° C. for 3 hours, then cooled, poured into 50 mL water and extracted with 3×30 mL ethyl acetate. The organic layers were combined, washed 2×20 mL water, dried (MgSO$_4$), stripped in vacuo, and the residue chromatographed on a 4 mm silica gel plate with 2:3 ether:hexane as eluant to yield 0.71 g (54%) of present title product.

This preparation was repeated on a 4.76× scale, without chromatography to produce 6.43 g (100%) of present title product.

PREPARATION 15

2-[(Dimethyl-t-butylsilyloxy)methyl]-5-[3-(2-phenyl-5-methyl-4-oxazolyl)propionyl]pyridine Title product of the preceding Preparation (6.43 g) was combined with 50 mL CH$_2$Cl$_2$, 50 mL trifluoroacetic acid added and the mixture stirred for 2 hours at room temperature. The solvent was stripped in vacuo and the residue combined with 250 mL saturated NaHCO$_3$ and extracted 3×250 mL ethyl acetate. The organic layers were combined, washed 1×250 mL water, dried (MgSO$_4$) and stripped in vacuo to yield 4.58 g of crude product. The latter was chromatographed on silica gel with 1:1 hexane:ethyl acetate to yield 2.53 g (48%) of purified title product.

PREPARATION 16

5-[3-(2-Phenyl-5-methyl-4-oxazolyl)propionyl]pyridine-2-methanol

Title product of the preceding Preparation (2.53 g) in 50 mL THF was diluted with 50 mL of 1N HCl and the mixture for 1 hour at room temperature, then stripped of THF in vacuo, and the aqueous residue neutralized with NaHCO$_3$ and extracted 3×100 mL ethyl acetate. The organic layers were combined, washed 2×50 mL water, dried (MgSO$_4$) and stripped in vacuo (ultimately at 50° C. under high vacuum to remove any byproduct silyl alcohol) to yield 1.8 g (97%) of present title product as a solid, mp 97°–99° C.

PREPARATION 17

5-[3-(2-Phenyl-5-methyl-4-oxazolyl)propionyl]pyridine-2-carbaldehyde

CH$_2$Cl$_2$ (2.5 mL) and oxalyl chloride (0.075 mL, 1.10 mmol) were combined and cooled to −60° C. DMSO (0.17 mL, 2.40 mmol) in 1 mL CH$_2$Cl$_2$ was added dropwise over 5 minutes as the stirred mixture was maintained at −60° C. After 1 minute, title product of the preceding Preparation (0.32 g, 1.00 mmol) in 1 mL CH$_2$Cl$_2$ was added over 2 minutes and stirring continued for 15 minutes at −60° C., at which time triethylamine (0.70 mL) was added, and the mixture warmed to room temperature, poured into 20 mL water, and the aqueous layer separated and extracted with 1×20 mL CH$_2$Cl$_2$. The organic layers were combined, dried (MgSO$_4$) and stripped to yield 0.34 g of crude product as a brown oil. The reaction was scaled, using 0.24 mL oxalyl chloride in 8 mL CH$_2$Cl$_2$, 0.55 mL DMSO in 3 mL CH$_2$Cl$_2$, 1.04 g of title product of the preceding Preparation in 3 mL CH$_2$Cl$_2$ and 2.26 mL of triethylamine to yield an additional 1.21 g of crude product. The crude products were combined and chromatographed on a 4 mm silica gel plate to yield 0.44 g (32%) of present title product, which, because of its poor stability was used immediately in further processing.

PREPARATION 18

Methyl 3-(5-Bromo-2-thienyl)-3-oxopropionate

Sodium hydride (1.95 g of 60% dispersion in oil, 0.045 mol), dimethyl carbonate (50 mL) and THF (40 mL) were added to a flame dried flask equipped with stirrer and dropping funnel. 2-Acetyl-5-bromothiophene (5.0 g, 0.024 mol) in 20 mL THF was added dropwise. The mixture was then heated at reflux for 2 hours, then poured into 250 mL of water, acidified to pH 2.0 with 1N HCl and extracted 3×200 mL ether. The organic layers were combined, dried (MgSO$_4$) and stripped to yield 6.4 g (99%) of present title product as an oil; tlc Rf 0.42 (CHCl$_3$).

By the same method, 2-acetyl-5-bromo-1-(methyl- or benzyl)pyrrole are converted to methyl 3-(5-bromo-1-(methyl- or benzyl)-2-pyrrolyl)-3-oxopropionate.

PREPARATION 19

Methyl 3-(5-Bromo-2-thienyl)-3-oxo-2-[(2-Phenyl-5-methyl-4-oxazolyl)methyl]propionate Title product of the preceding Preparation (4.43 g, 0.0168 mol) in 15 mL DMF was added dropwise to NaH (0.74 g of 60% dispersion in oil, previously washed with hexane, 0.0185 mol) in stirring in 15 mL DMF. Vigorous H$_2$ evolution was noted. After stirring for 0.75 hour at room temperature, by which time H$_2$ evolution had ceased, (2-phenyl-5-methyl-4-oxazolyl)methyl chloride (3.5 g, 0.0168 mol, was added in one portion, and the resulting mixture heated at 70° C. for 18 hours, cooled, diluted with 60 mL water, acidified to pH 3 with 1N HCl and extracted 3×90 mL 1:1 ether-ethyl acetate. The organic layers were combined, dried (MgSO$_4$) and stripped to yield 6.89 g of present title product is a dark colored oil of purity sufficient for use directly in the next step. If desired, the product was purified by silica gel chromatography using 1:19 ethyl acetate:hexane as eluant to produce more highly purified title product as a light colored oil.

By the same method, the other products of the preceding Preparation are converted to methyl 3-(5-bromo-1-(methyl- or benzyl)-2-pyrrolyl)-3-oxo-2-[(2-phenyl-5-methyl-4-oxazolyl)methyl]propionate.

PREPARATION 20

5-Bromo-2-[3-(2-phenyl-5-methyl-4-oxazolyl)propionyl]thiophene

To title product of the preceding Preparation (6.64 g, 0.0153 mol) in a 1:1 CH$_3$OH:THF (250 mL) was added 1N NaOH (125 mL) and the mixture stirred 4 hours at room temperature to yield intermediate 3-(5-bromo-2-thienyl)-3-oxo-2-(2-phenyl-5-methyl-4-oxazolyl)propionic acid. The mixture was made strongly acidic with 10% HCl (125 mL). The acidic mixture was stirred an additional 4 hours, then extracted 3×400 mL ethyl acetate. The organic layers were combined, dried (MgSO$_4$) and stripped to yield 4.7 g (82%) of present title product as an oil; tlc Rf 0.55 (CHCl$_3$).

By the same method, the other products of the preceding Preparation are converted to 5-bromo-2-[3-(2-phenyl-5-methyl-4-oxazolyl)propionyl]-1-(methyl- or benzyl)pyrrole.

PREPARATION 21

5-Bromo-2-[1-hydroxy-3-(2-phenyl-5-methyl-4-oxazolyl)propyl]thiophene

Title product of the preceding Preparation (0.25 g, 0.66 mmol) and NaBH$_4$ (9 mg, 0.22 mol) were combined in 5 mL ethanol and stirred at room temperature for 3 hours. The ethanol was stripped in vacuo and the residue dissolved in 5 mL water, adjusted to pH 2 with 1N HCl and extracted 3×5 mL CHCl$_3$. The organic layers were combined, dried (MgSO$_4$) and stripped to yield 0.18 g (73%) of present title product as an oil; tlc Rf 0.20 (CHCl$_3$), 0.40 (1:19 ethyl acetate:hexane).

By the same method, the other products of the preceding Preparation are converted to 5-bromo-2-[1-(dimethyl-t-butysilyloxy)-3-(2-phenyl-5-methyl-4-oxazolyl)propyl]-1-(methyl- or benzyl)pyrrole.

PREPARATION 22

5-Bromo-2-[1-(dimethyl-t-butylsilyloxy)-3-(2-phenyl-5-methyl-4-oxazolyl)propyl]thiophene Title product of the preceding Preparation (0.47 g, 1.24 mmol), imidazole (0.21 g, 3.12 mmol) and dimethyl-t-butylsilyl chloride (0.24 g, 1.56 mmol) were combined with 10 mL dry DMF and the mixture stirred at room temperature for 18 hours, then poured into 50 mL saturated NaHCO$_3$ and extracted 3×60 mL hexane. The organic layers were combined, washed 2×50 mL 5% HCl and 1×50 mL water, dried (MgSO$_4$) and stripped to yield 0.22 g (36%) of present title product as an oil; tlc Rf 0.75 (1:19 ethyl acetate:hexane).

PREPARATION 23

5-[1-(Dimethyl-t-butylsilyloxy)-3-(2-phenyl-5-methyl-4-oxazolyl)propyl]thiophene-2-carbaldehyde Title product of the preceding Preparation (0.22 g, 0.45 mmol) dissolved in 10 mL THF was cooled to −78° C. n-Butyllithium (0.25 mL of 2M in hexane; 0.49 mmol) was added via syringe and the resulting mixture stirred for 20 minutes at −78° C. DMF (0.3 mL) was added, and the mixture warmed to room temperature stirred for 15 minutes, poured into 25 mL water and extracted 3×30 mL ether. The organic layers were combined, dried (MgSO$_4$) and stripped in vacuo to yield 0.17 g (85%) of present title product as an oil.

By the same method, the other products of the preceding Preparation are converted to 5-[1-(dimethyl-t-butylsilyloxy)-3-(2-phenyl-5-methyl-4-oxazolyl)-propyl]-1-(methyl- or or benzyl)-2-carbaldehyde.

PREPARATION 24

5-(4-Acetylbenzyl)thiazolidine-2,4-dione

A solution of 3-(4-acetylphenyl)-2-bromopropanoic acid (87 g, 0.32 mol, prepared according to Cleland, Org. Synth. vol. 51, p. 1, 1971), and thiourea (48.7 g, 0.64 mol) in sulfolane (100 mL) was heated to 105°–110° C. for 5 hours. To this mixture was added a 2N HCl solution (162 mL) and the resulting solution was heated to 105°–110° C. overnight. After cooling and diluting with water, present title product was collected, washed with water and dried (75 g, 94%); mp 171°–172° C.

PREPARATION 25

4-[3-(2-Pyridyl)-2-propenoyl]benzaldehyde Diethyl Acetal

A solution of 4-(diethoxymethyl)acetophenone (1 g, 4.5 mmol) and 2-pyridinecarbaldehyde (0.64 mL, 6.75 mmol) in methanol (20 mL) and 1N NaOH (13.5 mL) was stirred at room temperature for 1 hour. The solution was diluted with water (30 mL) and extracted with ether (2×20 mL). The combined extracts were washed with brine, dried over magnesium sulfate and concentrated. The product was purified by flash-chromatography (hexane:ethyl acetate, 2:1) and obtained as an oil (0.78 g, 56%).

By the same method N-methylpyrrole-2-carbaldehyde and 1-benzyl imidazole-2-carbaldehyde are converted to 4-[3-(1-methyl-2-pyrrolyl)-2-propenoyl]benzaldehyde diethyl acetal and 4-[3-(1-benzyl-2-imidazolyl)-2-propenoyl]benzaldehyde.

PREPARATION 26

4-[3-(2-Pyridyl)propionyl]benzaldehyde

A solution of title product of the preceding Preparation (0.78 g, 2.5 mmol) in ethanol (50 mL) containing 10% palladium on carbon (80 mg) was hydrogenated in a Parr apparatus at 50 psig for 1 hour. The catalyst was recovered by filtration and the solution concentrated in vacuo.

The resulting oil was dissolved in THF (10 mL) and 1N HCl (5 ml) and the solution was stirred at room temperature overnight, then neutralized with 1N NaOH (5 mL), diluted with water (10 mL) and extracted with ethyl acetate (3×15 mL). The combined extracts were washed with water (15 mL) and brine (15 mL), dried over magnesium sulfate and concentrated in vacuo to give present title product as an oil (345 mg, 58%).

By the same method, the other products of the preceding Preparation are converted to 4-[3-(1-methyl-2-pyrrolyl)propionyl]benzaldehyde and 4-[3-(2-imidazolyl)propionyl]benzaldehyde.

PREPARATION 27

4,5-Dimethyl-2-(4-methylphenyl)oxazole N-Oxide Hydrochloride

At 0°–5° C., dry HCl was bubble through a solution of p-tolualdehyde (125 g, 1.04 mol) and 3-oximino-2-butanone (95.6 g, 0.946 mol) in 350 ml of ethyl acetate. Title product was precipitated by dilution with ether and recovered by filtration with ether wash, 207 g; mp 198°–200° C. (dec).

PREPARATION 28

[5-Methyl-2-(4-methylphenyl)-4-oxazolyl]methyl Chloride $POCl_3$ (172 g, 104 ml, 1.13 mol) in 1 liter $CHCl_3$ was added dropwise to a solution of title product of the preceding Preparation (206.7 g, 0.86 mol) in 1 liter of $CHCl_3$, maintaining the temperature below 15° C. with an ice-water bath. The resulting solution was stirred at ambient temperature for 2 hours and then heated at reflux for 2.5 hours, cooled, adjusted to pH 9 with conc. $NH_4OH$, and poured into 1 liter of water. The organic layer was separated and washed $3 \times 1$ liter water, dried ($MgSO_4$), stripped to 208 g of solids, and the residue recrystallized from hexane to yield 162 g of title product as a white solid; mp 91°–93° C.

PREPARATION 29

1-(5-Bromo-2-thienyl)-3-(5-methyl-2-(4-methylphenyl)-4-oxazolyl)-1-propanone NaH (60% dispersion in oil, 32.5 g, 0.81 mol) was combined with 500 ml of dry dimethylformamide. A solution of methyl 2-(5-bromo-2-thenoyl)acetate (178 g, 0.677 mol) in 500 ml dimethylformamide was added dropwise over about 1 hour, maintaining a slow but steady evolution of $H_2$. Following that, a solution of title product of the preceding Preparation (150 g, 0.677 mol) in 500 ml dimethylformamide was added portionwise over 30 minutes. The resulting solution was heated at 100° C. for 15 hours, cooled, poured into 12 liters of $H_2O$ and extracted $3 \times 2.7$ liters of ethyl acetate. The organic layers were combined, stripped and the residual oil taken up in 3 liters of 4:1 $CH_3COOH$:conc. HCl, refluxed for 3.5 hours, cooled, poured into 5 liters of $H_2O$, the pH adjusted to 8.5 with $Na_2CO_3$ and extracted $3 \times 4$ liters of ethyl acetate. The organic layers were combined, dried ($MgSO_4$), stripped to 218 g of oil and chromatographed on 1.5 kg silica gel using 1:13 ethyl acetate:hexane as eluant to yield title product as a solid, 119.3 g, mp 118°–119° C.

PREPARATION 30

1-(5-Bromothienyl)-3-(5-methyl-2-(4-methylphenyl)-4-oxazolyl)-1-propanol

By the method of Preparation 21, title product of the preceding Preparation (119.3 g, 0.305 mol) was reduced to present title product as a gummy solid; 120.4 g, tlc Rf 0.55 (1% $CH_3OH$ in $CHCl_3$).

PREPARATION 31

5-Bromo-2-[1-(dimethyl-t-butylsilyloxy)-3-(2-(4-methylphenyl)-5-methyl-4-oxazolyl)propyl]thiophene By the method of Preparation 22, the product of the preceding Preparation (119.6 g, 0.305 mol) was converted to present title product purified by chromatography on silica gel using 1:19 ethyl acetate:hexane as eluant, 134 g; oil; the Rf 0.75 (1:9 ethyl acetate:hexane).

PREPARATION 32

5-[1-(Dimethyl-t-butylsilyloxy)-3-(2-(4-methylphenyl)-5-methyl-4-oxazolyl)propyl]thiophene-2-carbaldehyde By the method of Preparation 23, the product of the preceding Preparation (133.3 g, 0.263 mol) was converted to present title product, initially as an oil which crystallized on standing, 117.7 g; mp 122°–124° C.

We claim:

1. A compound of the formula

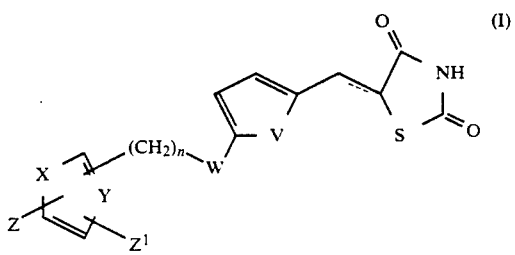

wherein
the dotted line represents a bond or no bond;
V is $-CH=CH-$, $-N=CH-$, $-CH=N-$ or S;
W is $CH_2$, CHOH, CO, or $CH=CH$;
X is S, O, or $NR^1$;
Y is CH or N;
Z is phenyl, naphthyl, pyridyl, furyl, thienyl or phenyl mono- or disubstituted with the same or different groups which are $(C_1-C_3)$lkyl, trifluoromethyl, $(C_1-C_3)$alkoxy, fluoro, chloro or bromo;
$Z^1$ is hydrogen or $(C_1-C_3)$alkyl;
R and $R^1$ are each independently is hydrogen or methyl; and
n is 1, 2 or 3;
a pharmaceutically acceptable cationic salt thereof; or a pharmaceutically acceptable acid addition salt thereof when the compound contains a basic nitrogen.

2. A compound of claim 1 wherein the dotted line represents no bond.

3. A compound of claim 2 wherein W is CO or CHOH.

4. A compound of claim 3 wherein V is $-CH=CH-$, $-CH=N-$ or S, and n is 2.

5. A compound of claim 4 wherein X is O and Y is N, X is S and Y is N, or X is S and Y is CH.

6. A compound of claim 5 wherein X is O and Y is N forming an oxazol-4-yl group.

7. A compound of claim 6 wherein Z is (2-thienyl), (2-furyl), phenyl or substituted phenyl.

8. A compound of claim 7 wherein Z is 2-phenyl and $Z^1$ is 5-methyl.

9. The compound of claim 8 wherein V is $-CH=N-$ and W is CHOH.

10. The compound of claim 8 wherein V is S and W is CHOH.

11. The compound of claim 8 wherein V is S and W is CO.

12. The compound of claim 8 wherein V is $-CH=CH-$ and W is CO.

13. A compound of claim 5 wherein X is O and Y is N forming an oxazol-5-yl group.

14. A compound of claim 5 wherein X is S and Y is N forming a thiazol-4-yl or a thiazol-5-yl group.

15. A compound of claim 5 wherein X is O and Y is CH forming a fur-2-yl group.

16. A compound of claim 2 wherein W is CH=CH and n is 1.

17. A compound of claim 16 wherein V is —CH=CH— or S.

18. A compound of claim 17 wherein X is O and Y is N forming an oxazol-4-yl group.

19. The compound of claim 18 wherein V is S, Z is 2-(4-methylphenyl) and $Z^1$ is 5-methyl.

20. The compound of claim 18 wherein V is —CH=CH—, Z is 2-phenyl and $Z^1$ is 5-methyl.

21. A pharmaceutical composition which comprises a blood glucose lowering amount of a compound of claim 1 and a pharmaceutically acceptable carrier.

22. A pharmaceutical composition which comprises a blood glucose lowering amount of a compound of claim 2 and a pharmaceutically acceptable carrier.

23. A pharmaceutical composition which comprises a blood glucose lowering amount of a compound of claim 3 and a pharmaceutically acceptable carrier.

24. A pharmaceutical composition which comprises a blood glucose lowering amount of a compound of claim 18 and a pharmaceutically acceptable carrier.

25. A method of lowering the blood glucose in a hyperglycemic mammal which comprises administering to said mammal a blood glucose lowering effective amount of a compound of claim 1.

26. A method of lowering the blood glucose in a hyperglycemic mammal which comprises administering to said mammal a blood glucose lowering effective amount of a compound of claim 2.

27. A method of lowering the blood glucose in a hyperglycemic mammal which comprises administering to said mammal a blood glucose lowering effective amount of a compound of claim 3.

28. A method of lowering the blood glucose in a hyperglycemic mammal which comprises administering to said mammal a blood glucose lowering effective amount of a compound of claim 16.

29. A pharmaceutical composition which comprises a blood cholesterol lowering amount of a compound of claim 1 and a pharmaceutically acceptable carrier.

30. A pharmaceutical composition which comprises a blood cholesterol lowering amount of a compound of claim 2 and a pharmaceutically acceptable carrier.

31. A pharmaceutical composition which comprises a blood cholesterol lowering amount of a compound of claim 3 and a pharmaceutically acceptable carrier.

32. A pharmaceutical composition which comprises a blood cholesterol lowering amount of a compound of claim 16 and a pharmaceutically acceptable carrier.

33. A method of lowering the blood cholesterol in a hypercholesterolemic mammal which comprises administering to said mammal a blood cholesterol lowering effective amount of a compound of claim 1.

34. A method of lowering the blood cholesterol in a hypercholesterolemic mammal which comprises administering to said mammal a blood cholesterol lowering effective amount of a compound of claim 2.

35. A method of lowering the blood cholesterol in a hypercholesterolemic mammal which comprises administering to said mammal a blood cholesterol lowering effective amount of a compound of claim 3.

36. A method of lowering the blood cholesterol in a hypercholesterolemic mammal which comprises administering to said mammal a blood cholesterol lowering effective amount of a compound of claim 16.

37. The compound of claim 8 wherein V is —CH=CH— and W is CHOH.

* * * * *